United States Patent [19]

Clark et al.

[11] Patent Number: 4,642,378
[45] Date of Patent: Feb. 10, 1987

[54] ARYLALKYL AMINES USEFUL FOR LOWERING INTRAOCULAR PRESSURE

[75] Inventors: Robin D. Clark, Palo Alto; L. David Waterbury, San Mateo, both of Calif.

[73] Assignee: Syntex (U.S.A.) Inc., Palo Alto, Calif.

[21] Appl. No.: 722,046

[22] Filed: Apr. 11, 1985

[51] Int. Cl.$^4$ .......................................... C07C 127/19
[52] U.S. Cl. ...................... 564/51; 564/157; 564/164; 564/165
[58] Field of Search ...................... 564/50, 51; 514/597

[56] References Cited

U.S. PATENT DOCUMENTS

| | | | |
|---|---|---|---|
| 2,050,557 | 8/1936 | Bockmuhl et al. | 564/51 X |
| 2,796,783 | 8/1976 | Cox et al. | 564/154 |
| 3,644,520 | 2/1972 | Hartley et al. | 564/220 |
| 3,689,524 | 9/1972 | Jack et al. | 564/50 |
| 3,763,232 | 10/1973 | Kaiser et al. | 564/51 |
| 3,803,230 | 4/1974 | Jack et al. | 564/165 |
| 3,862,222 | 1/1975 | Kaiser et al. | 564/51 |
| 4,063,025 | 12/1977 | Murakami et al. | 564/51 |
| 4,127,674 | 11/1978 | Leopold | 424/324 |
| 4,146,645 | 3/1979 | Schromm et al. | 564/51 X |
| 4,287,211 | 9/1981 | Ferrari et al. | 564/51 |
| 4,396,627 | 8/1983 | Ainsworth et al. | 564/51 |
| 4,404,222 | 9/1983 | Baker et al. | 424/304 |
| 4,482,566 | 11/1984 | Hirai et al. | 564/220 X |
| 4,507,320 | 3/1985 | DeMarinis et al. | 514/605 |

FOREIGN PATENT DOCUMENTS 7014960  4/1972  Netherlands .................. 564/50

OTHER PUBLICATIONS

T. Nogrady, "Medicinal Chemistry, A Biochemical Approach", Chapter 4.3.
A. M. Barrett, Design of β—Blocking Drugs in "Drug Design", vol. III, pp. 205-228.

Primary Examiner—Charles F. Warren
Assistant Examiner—C. S. Greason
Attorney, Agent, or Firm—Grant D. Green; Tom M. Moran; Alan M. Krubiner

[57] ABSTRACT

Intraocular hypertensive diseases such as glaucoma are treated with compounds represented by formula I

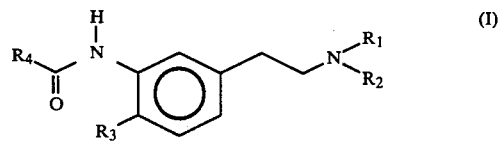

or a pharmaceutically acceptable acid addition salt thereof, wherein
$R_1$ is alkyl of two to four carbon atoms;
$R_2$ is $-(CH_2)_n-C_6H_4-R_5$; where
  n is an integer from 1 to 4; and
  $R_5$ is $-H$, $-OH$, halo, lower alkyl, lower alkoxy, ureido, lower alkyl-ureido, lower alkyl-amido, or formamido;
$R_3$ is hydro or hydroxy; and
$R_4$ is hydro, lower alkyl, amino, or lower alkylamino.

1 Claim, No Drawings

ARYLALKYL AMINES USEFUL FOR LOWERING INTRAOCULAR PRESSURE

BACKGROUND OF THE INVENTION

1. Field of the Invention

This invention relates to arylalkyl aminoethylaniline derivatives and the pharmaceutically acceptable acid addition salts thereof. These compounds are administered to the eye to lower intraocular pressure. The invention also relates to a pharmaceutically acceptable composition containing an effective amount of at least one of the compounds in combination with a suitable excipient, the composition being useful for the treatment of intraocular hypertensive diseases such as glaucoma in mammals.

2. Related Disclosures

Certain alkyl and dialkyl aminoethylanilines are known. See, for example, U.S. Pat. Nos. 4,287,211, 4,404,222, 3,803,230, and 3,689,524 and German Pat. No. 2,612,354. A novel class of arylalkyl aminoethylaniline derivatives has now been prepared.

SUMMARY OF THE INVENTION

The first aspect of this invention is a compound of formula I useful in the treatment of intraocular hypertension.

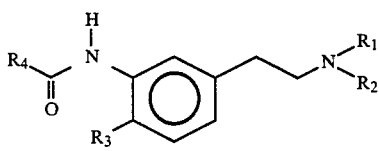

or a pharmaceutically acceptable acid addition salt thereof, wherein $R_1$ is alkyl of two to four carbon atoms;
$R_2$ is —$(CH_2)_n$—$C_6H_4$—$R_5$; where
  n is an integer from 1 to 4; and
  $R_5$ is —H, —OH, halo, lower alkyl, lower alkoxy, ureido, lower alkyl-ureido, lower alkyl-amido, or formamido;
$R_3$ is hydro or hydroxy; and
$R_4$ is hydro, lower alkyl, amino, or lower alkylamino.

Another aspect of the invention is the method of treatment of intraocular hypertensive diseases such as glaucoma with a compound of formula I.

Another aspect of the invention is a composition useful in the treatment of intraocular hypertensive diseases such as glaucoma in mammals which composition comprises an effective amount of at least one compound chosen from those represented by formula I above or a pharmaceutically acceptable acid addition salt thereof and a pharmaceutically suitable excipient.

Another aspect of the invention is the use of a compound of formula I, or a pharmaceutically acceptable acid addition salt thereof, to prepare a composition useful in the treatment of intraocular hypertensive diseases such as glaucoma in mammals.

DETAILED DESCRIPTION AND PREFERRED EMBODIMENTS

The broadest aspect of the present invention is the compound of formula I, or a pharmaceutically acceptable acid addition salt thereof:

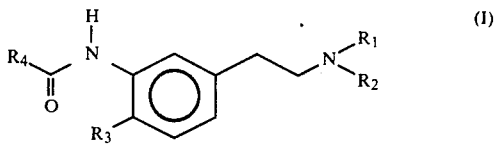

wherein $R_1$ is alkyl of two to four carbon atoms; and
$R_2$ is —$(CH_2)_n$—$C_6H_4$—$R_5$; where
  n is an integer from 1 to 4; and
  $R_5$ is —H, —OH, halo, lower alkyl, lower alkoxy, ureido, lower alkyl-ureido, lower alkyl-amido, or formamido;
$R_3$ is hydro or hydroxy; and
$R_4$ is hydro, lower alkyl, amino, or lower alkylamino.

One preferred subgenus of compounds of formula I is that wherein $R_3$ is hydro, particularly where n is 2. A preferred class of the invention is that wherein $R_4$ is amino. A preferred compound is that wherein $R_2$ is phenethyl and $R_1$ is n-propyl. Another preferred compound is that wherein $R_5$ is 3-ureido and $R_1$ is n-propyl. Another preferred compound is that wherein $R_5$ is hydroxy and $R_1$ is n-butyl. Another preferred class of the invention is the class wherein n is 4. A preferred subclass of the invention is that wherein $R_4$ is methyl. A preferred compound is that wherein $R_5$ is hydro and $R_1$ is n-propyl.

Another preferred subgenus of compounds of formula I is that wherein $R_3$ is hydroxy, particularly where $R_4$ is amino. A preferred compound is that wherein $R_2$ is phenethyl and $R_1$ is n-propyl. Another preferred compound is that wherein $R_5$ is 3-hydroxy and $R_1$ is n-propyl.

Another aspect of the invention is the method of treating a mammal with elevated intraocular pressure by administering directly to the eye of said mammal a compound of formula I.

One preferred subgenus of compounds of formula I is that wherein $R_3$ is hydro, particularly where $R_4$ is amino. A preferred compound is that wherein $R_2$ is phenethyl and $R_1$ is n-propyl. Another preferred compound is that wherein $R_2$ is 3-ureidophenethyl and $R_1$ is n-propyl.

Another aspect of the invention is a pharmaceutical composition for treating intraocular hypertension comprising a pharmaceutically acceptable, non-toxic carrier and a therapeutically effective amount of a compound of formula I.

Another aspect of the invention is the use of a compound of formula I, or a pharmaceutically acceptable acid addition salt thereof, to prepare a composition useful in the treatment of intraocular hypertensive diseases such as glaucoma in mammals.

As used in the specification and the appended claims, unless specified to the contrary, the following terms have the meaning indicated:

The term "lower alkyl" refers to a straight or branched chain monovalent substituent consisting solely of carbon and hydrogen, containing no unsaturation and having from one to four carbon atoms. Examples of lower alkyl groups are methyl, ethyl, n-propyl, i-propyl, n-butyl, i-butyl, s-butyl and t-butyl.

The term "—$C_6H_4$—" refers to a disubstituted phenyl group.

The term "ureido" refers to —$NHCONH_2$.

The term "formamido" refers to —NHCHO.

The term "lower alkyl-amido" refers to —NHCOR, where R is lower alkyl as defined above.

The term "halo" refers to chloro, bromo, or iodo.

The term "pharmaceutically acceptable acid addition salts" refers to salts of the subject compounds which possess the desired pharmacological activity and which are neither biologically nor otherwise undesirable. These salts are formed with inorganic acids such as hydrochloric acid, hydrobromic acid, sulfuric acid, nitric acid or phosphoric acid; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The term "direct administration" means administration directly to the eye of the subject, and excludes general systemic administration. Direct administration includes, without limitation, topical application of aqueous solutions and ointments, administration of controlled release devices, and subconjunctival injection.

The term "treatment" as used herein covers any treatment of an intraocular hypertensive disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

ADMINISTRATION AND FORMULATION

Ophthalmic preparations are sterile products for either topical application to the eyes or instillation into the space (cul-de-sac) between the eyeball and the eyelids. Presently available ophthalmic preparations include solutions, suspensions, ointments, and controlled release devices. Presently available topical treatment of eye diseases include topically applied ophthalmic drops, solutions, suspensions or ointment or their subconjunctival injection.

The composition of this invention comprises a compound of this invention or a salt thereof in admixture with an ophthalmologically acceptable excipient.

An excipient is ophthalmologically acceptable if it is non-irritating and non-toxic.

The ophthalmic composition may be aqueous or non-aqueous, and it may be in the form of a solution, suspension, gel, ointment, slow release polymer, or other. The amount of active ingredient will vary with the particular formulation and disease state but generally will be between 0.001–10% wt/vol of active ingredient per individual application dose.

Pharmaceutical ophthalmic compositions are typically provided as sterilized aqueous solutions (i.e. eyedrops) containing 0.001% to 10% wt/vol.; most preferably 0.005% to 1% of the active ingredient, along with a suitable buffer, stabilizer, and preservative. The total concentration of solutes should be such that, if possible, the resulting solution is isotonic with the lacrimal fluid (though this is not absolutely necessary) and has an equivalent pH (in the range of pH 6–8). Typical preservatives/sterilants are phenylmercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8–8.0, making a final volume adjustment with additional water, and sterilizing the preparation using methods known to those skilled in the art.

The dosage level of the resulting composition will, of course, depend on the concentration of the drops, the condition of the subject and the individual magnitude of responses to treatment. However, typical dosage ranges might be about 2–10 drops of 0.1% solution of active ingredient once to three times per day.

Most ophthalmic solutions and suspensions contain an aqueous rather than an oily vehicle. Ophthalmic ointments usually contain a white petrolatum-mineral oil base, often including anhydrous lanolin, while some have a polyethylene-gelled mineral oil base.

Solutions are the most commonly used type of preparation for the local medication of eyes. They are easily instilled and rarely cause adverse reactions. The vehicle should not interfere with vision and should not interfere with regeneration of the corneal epithelium.

Suspensions have the advantage of more extended action and the disadvantage that it is difficult to avoid the presence of a few particles which are large enough to cause irritation.

Eye ointments are sterile preparations for application to the conjunctival sac or lid margin. They have advantages of more prolonged contact and effect, minimal irritation on initial installation, slower movement into lacrimal ducts, greater storage stability, and less likelihood of contamination problems. Their disadvantages are that they produce a film over the eye thereby blurring vision, and they may interfere with the firm attachment of new corneal epithelial cells to their normal base. Ointments affect the outside and edges of the eyelids, the conjunctiva, the cornea, and the iris, depending on their ability to penetrate the outer covering of the eyeball.

Ophthalmic ointments comprising active ingredients can be used on the outside and edges of the eyelids, the conjunctiva, the cornea, and the iris. Most ophthalmic ointments are prepared with a base of white or yellow petrolatum and mineral oil, often with added anhydrous lanolin or polyethylene-gelled mineral oil. Whichever base is selected, it must be nonirritating to the eye, permit diffusion of the drug throughout the secretions bathing the eye, and retain the activity of the medicament for a reasonable period of time under proper storage conditions.

Compounds of this invention may also be administered by other nonsystemic modes. Ophthalmic packs may be used to give prolonged contact of the solution with the eye. For example, a cotton pledget saturated with an ophthalmologically suitable solution of a compound of this invention may be inserted into the superior or inferior fornix. Medicated controlled release ophthalmic disks may produce effects both more intense and prolonged than solutions. See, e.g., U.S. Pat. No. 4,190,642, incorporated herein by reference, which discloses a controlled-release device for administering compounds to the eye, which may be useful in the practice of this invention.

The compounds of the invention may also be administered by the way of iontophoresis. This procedure keeps the solution in contact with the cornea in an eyecup bearing an electrode. Diffusion of the active compound is effected by difference of electrical potential. *Reming-* ton's *Pharmaceutical Sciences*, 15th Ed., 1489–1504, (1975).

PREPARATION OF THE INVENTION

Compounds of formula I are prepared by the reaction sequence shown below.

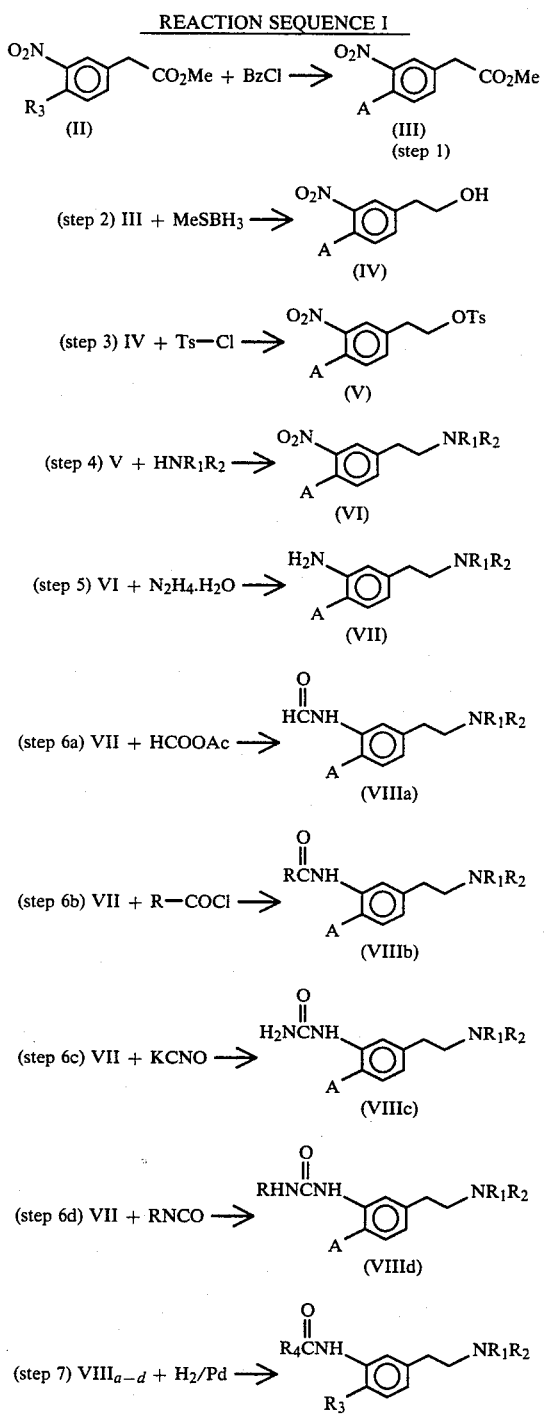

wherein $R_1$, $R_2$, $R_3$, and $R_4$ are as defined above in the broadest aspect of the invention, Ts is tosyl (p-toluenesulfonyl), A is benzyloxy (BzO) or hydro, BzCl is benzyl chloride, and R is lower alkyl.

When compounds in which $R_3$ is hydro and $R_5$ is not hydroxy are desired, steps (1) and (7) are not necessary and are omitted; in such cases step (6a, b, c, or d) is the final step.

For compounds in which $R_3$ is hydroxy, 4-hydroxy-3-nitrophenylacetic acid (II), available, e.g., from Aldrich Chemical Co., is first converted to the methyl ester, then reacted with an equimolar amount of benzyl chloride, also available, e.g., from Aldrich Chemical Co., using the Williamson Ether Synthesis to yield a hydroxy-protected methyl 4-benzyloxy-3-nitrophenylacetate (III, A=BzO). The reaction is usually performed using potassium carbonate in refluxing acetonitrile or ethanol. (Step 1.)

The protected nitrophenylacetic acid ester (III, A=BzO) is then reduced, using borane-methyl sulfide in a tetrahydrofuran (THF) solution at room temperature. After acidification with HCl in methanol, the solution is evaporated, and the product 4-benzyloxy-3-nitrophenylethanol (IV, A=BzO) extracted from aqueous sodium carbonate with diethyl ether ($Et_2O$). Similarly, compounds in which A=H may be prepared by the same method, substituting 3-nitrophenylacetic acid (III, A=H) for methyl 4-benzyloxy-3-nitrophenylacetate. 3-Nitrophenylacetic acid is available commercially from e.g. Aldrich Chemical Co. (Step 2.)

The 4-benzyloxy-3-nitrophenylethanol (IV, A=BzO) is then reacted with a molar excess of p-toluenesulfonyl chloride in pyridine at 0° C. to produce a 4-benzyloxy-3-nitrophenylethyl tosylate (V, A=BzO). The tosylate (V, A=BzO) is extracted using ethyl acetate. Similarly, compounds in which A=H may be prepared by the same method, substituting 3-nitrophenylethanol (IV, A=H) for 4-benzyloxy-3-nitrophenylethanol. (Step 3.)

The desired arylalkyl-alkyl amine is then prepared by reaction of a suitable arylalkanol with p-toluenesulfonyl chloride to form the tosylate, followed by reaction with a suitable alkyl amine in dimethylformamide (DMF) at 65° C.

The tosylate (V, A=BzO) is reacted with an equimolar amount of the desired arylalkyl-alkyl amine in DMF at 65° C. to produce a 2-benzyloxy-5-(N-alkyl-N-arylalkyl)aminoethylnitrobenzene (VI, A=BzO). Similarly, compounds in which A=H may be prepared by the same method, substituting 3-nitrophenylethyl tosylate (V, A=H) for 4-benzyloxy-3-nitrophenylethyl tosylate. (Step 4.)

The 2-benzyloxy-5-(N-alkyl-N-arylalkyl)aminoethylnitrobenzene (VI, A=BzO) is then reduced to a 2-benzyloxy-5-(N-alkyl-N-arylalkyl)aminoethylaniline derivative (VII, A=BzO) with hydrazine and Raney nickel in refluxing ethanol at ambient pressure with an equimolar amount of hydrogen, using the general method known for other unrelated compounds. See, e.g., *Introduction to Organic Chemistry*, by Andrew Streitwieser, Jr., and Clayton H. Heathcock, Ch. 32, p. 961 (1976). Similarly, compounds in which A=H may be prepared by the same method, substituting 3-(N-alkyl-N-arylalkyl)aminoethylnitrobenzene (VI, A=H) for 2-benzyloxy-5-(N-alkyl-N-arylalkyl)aminoethylnitrobenzene. (Step 5.)

The sequence is completed by reacting the aniline derivative with an equimolar amount of the appropriate reactive formyl derivative, carboxylic acid derivative, isocyanate, or alkylisocyanate.

If a formamido derivative (VIIIa, A=H or BzO) is desired, the novel aniline derivative (VII, A=H or BzO) is reacted at 0° C. with an equimolar amount of an appropriate reactive formyl derivative (e.g., formic acetic anhydride, which may be generated in situ from sodium formate and acetyl chloride, which are commercially available) in an appropriate aprotic base. (Step 6a.)

To produce a compound in which $R_4$ is lower alkyl (VIIIb, A=H or BzO), the aniline derivative (VII, A=H or BzO) is reacted at 25° C. with an equimolar amount of an appropriate reactive carboxylic acid derivative, especially an acyl halide, in an appropriate aprotic base. Carboxylic acid chlorides are available commercially, or may be prepared from commercially available carboxylic acids by methods known in the art. (Step 6b.)

To produce a ureidobenzene derivative (VIIIc, A=H or BzO), the aniline derivative (VII, A=H or BzO) is reacted at 25° C. with an equimolar amount of an appropriate cyanate salt, e.g., potassium cyanate, in an acidic medium. (Step 6c.)

To produce an alkyl ureidobenzene derivative (VIIId, A=H or BzO), the aniline derivative (VII, A=H or BzO) is reacted at 25° C. with an equimolar amount of an appropriate alkyl isocyanate, using the general method known in the art for unrelated compounds. See, e.g., *Introduction to Organic Chemistry*, Streitwieser & Heathcock, Ch. 27, p. 801. Alkyl isocyanates may be obtained commercially, or may be produced by reacting the appropriate alkyl halide with a reactive cyanate salt. (Step 6d.)

In compounds wherein neither $R_3$ nor $R_5$ is hydroxy, Step 6a, b, c, or d produces the compound of formula I directly. Where $R_3$ or $R_5$ is hydroxy, it is necessary to remove the benzyloxy protecting group. This may be accomplished by the method described in *Catalytic Hydrogenation in Organic Synthesis: Procedures and Commentary*, M. Freifelder, (Wiley, 1978), p. 109, e.g., by catalytic hydrogenolysis of the penultimate compound (VIIIa-d) using palladium on carbon in methanol at ambient temperature and a pressure of 2 atmospheres, affording the compound of the invention (I).

In summary, compounds of formula I are prepared by the following methods:

Compounds of formula I in which neither $R_3$ nor $R_5$ is hydroxy are prepared by reacting a compound of formula VII (where A=H) with an appropriate reactive formyl derivative, carboxylic acid derivative, isocyanate salt, or alkylisocyanate, to produce the corresponding formanilide derivative, alkanylanilide derivative, ureidobenzene derivative, or alkylurea derivative. These reactions may be performed at atmospheric pressure, and at temperatures between the freezing and boiling points of the solvents employed, preferably between about −5° C. and about 110° C., and most preferably at about 25° C.

Compounds of formula I in which $R_3$ or $R_5$ is OH are prepared by performing the same procedure using a compound of formula VII (where A=BzO), followed by removal of the protecting benzyloxy group, e.g., by catalytic hydrogenolysis with $H_2$ over palladium on carbon at about 60° C. and pressure of about two atmospheres.

Pharmaceutically acceptable acid addition salts of the compounds of formula I are prepared by reacting a free base of formula I with an appropriate acid. Free bases of formula I are prepared by reacting an acid addition salt of a compound of formula I with an appropriate base.

The following specific description is given to enable those skilled in the art to come clearly understand and practice the invention. It should not be considered as a limitation upon the scope of the invention, but merely as being illustrative and representative thereof.

PREPARATION 1

(Preparation of Compounds of Formula III Wherein A is Benzyloxy)

(Step 1)

The carboxy function of 4-hydroxy-3-nitrophenylacetic acid (II) is first protected by forming the methyl ester using HCl in methanol, the procedure for which is known in the art. Then, 10.5 g methyl 4-hydroxy-3-nitrophenylacetate and 10 g benzyl chloride are reacted with 5 g potassium carbonate in ethanol. The product is extracted with ether.

PREPARATION 2

(Preparation of Compounds of Formula IV Wherein A is Hydrogen or Benzyloxy)

(Step 2)

(A)

40 g of 3-nitrophenylacetic acid was added to a solution of 26 ml of 10M borane-methyl sulfide in 200 ml of THF, and the mixture was stirred at 25° C. for 3 hr. The solution was then acidified with HCl in methanol, followed by evaporation of the solvent. The product 3-nitrophenylethanol (IV, A=H) was partitioned between diethyl ether ($Et_2O$) and aqueous sodium carbonate, and the $Et_2O$ layer dried over sodium sulfate. Evaporation of the $Et_2O$ afforded 34.8 g of 3-nitrophenylethanol (IV, A=H) as an oil.

(B)

Similarly, proceeding as in Part A above, but substituting methyl 4-benzyloxy-3-nitrophenylacetate for 3-nitrophenylacetic acid, the compound 4-benzyloxy-3-nitrophenylethanol (IV, A=BzO) is produced.

PREPARATION 3

(Preparation of Compounds of Formula V)

(Step 3)

(A)

34.6 g of 3-nitrophenylethanol (IV, A=H) was added to 41 g of p-toluenesulfonyl chloride in 200 ml of pyridine at 0° C. and allowed to stand for 24 hr. Water was added, and the mixture extracted with ethyl acetate. The ethyl acetate extract was washed with 5% HCl, water, and brine, dried over $Na_2SO_4$, and evaporated to a residue. The residue was recrystallized from $Et_2O$ to afford 34 g of 3-nitrophenylethyltosylate (V, A=H).

(B)

Similarly, proceeding as in Part A above, but substituting 4-benzyloxy-3-nitrophenylethanol for 3-nitrophenylethanol, the compound 4-benzyloxy-3-nitrophenylethyltosylate (V, A=BzO) is produced.

PREPARATION 4

(Preparation of $HNR_1R_2$)

(A)

25.3 g of phenethanol (available commercially from, e.g., Aldrich Chemical Co.) is added to 41 g of p-toluenesulfonyl chloride in 200 ml of pyridine at 0° C. and allowed to stand for 24 h. Water is added, and the mixture extracted with ethyl acetate. The ethyl acetate extract was washed with 5% HCl, water, and brine, dried over Na$_2$SO$_4$, and evaporated to a residue. The resulting tosyloxyethylbenzene is then stirred with 12.2 g of n-propylamine in 100 ml of DMF at 65° C. for one hour. The solution is diluted with water and acidified with HCl. The mixture is then washed with Et$_2$O, basified with NH$_4$OH, and extracted with ethyl acetate. Evaporation of the solvent (after drying over Na$_2$SO$_4$) produces N-propyl-N-phenethylamine (HNR$_1$R$_2$).

(B)

Similarly, proceeding as in Part A above, but substituting ethylamine and butylamine for propylamine, the following compounds are produced:
N-ethyl-N-phenethylamine;
N-butyl-N-phenethylamine.

(C)

Similarly, proceeding as in Parts A and B above, but substituting 4-benzyloxyphenethanol, 3-nitrophenethanol, 4-phenylbutanol, 3-nitro-1-hydroxymethylbenzene, 4-methylphenethanol, 4-butylphenethanol, 3-methoxyphenethanol, and 4-butoxyphenethanol for phenethanol, the following compounds are produced:
N-propyl-N-(4-benzyloxyphenethyl)amine;
N-butyl-N-(4-benzyloxyphenethyl)amine;
N-ethyl-N-(3-nitrophenyl)ethylamine;
N-propyl-N-phenylbutylamine;
N-ethyl-N-(3-nitrophenyl)methylamine;
N-butyl-N-(4-methylphenyl)ethylamine;
N-propyl-N-(4-butylphenethyl)amine;
N-propyl-N-(3-methoxyphenethyl)amine; and
N-propyl-N-(3-butoxyphenethyl)amine.

PREPARATION 5

(Preparation of Compounds of Formula VI)

(Step 4)

(A)

A mixture of 18.8 g of 3-nitrophenylethyl-2-tosylate and 25 ml of N-propyl-N-phenethylamine in 100 ml of DMF was stirred at 65° C. for 12 hr. The solution was diluted with water and acidified with HCl. The mixture was then washed with Et$_2$O, basified with NH$_4$OH, and extracted with ethyl acetate. Evaporation of the solvent (after drying over Na$_2$SO$_4$) produced 10.1 g of 3-(2-N-propyl-N-phenethylaminoethyl)nitrobenzene (VI, A=H).

(B)

Similarly, proceeding as above, substituting the compounds prepared in Preparation 4 (B–C) for N-propyl-N-phenethylamine, the following compounds (VI, A=H) are prepared:
3-(2-N-ethyl-N-phenethylaminoethyl)nitrobenzene;
3-(2-N-butyl-N-benzylaminoethyl)nitrobenzene;
3-[2-N-propyl-N-(4-benzyloxyphenethyl)aminoethyl]nitrobenzene;
3-[2-N-butyl-N-(4-benzyloxyphenethyl)aminoethyl]nitrobenzene;
3-[2-N-ethyl-N-(3-nitrophenyl)ethylaminoethyl]nitrobenzene;
3-(2-N-propyl-N-phenylbutylaminoethyl)nitrobenzene;
3-[2-N-ethyl-N-(3-nitrophenyl)methylaminoethyl]nitrobenzene;
3-[2-N-butyl-N-(4-methylphenyl)ethylaminoethyl]nitrobenzene;
3-[2-N-propyl-N-(4-aminophenethyl)aminoethyl]nitrobenzene;
3-[2-N-propyl-N-(4-butylphenyl)methylaminoethyl]nitrobenzene;
3-[2-N-propyl-N-(3-methoxyphenyl)ethylaminoethyl]nitrobenzene; and
3-[2-N-propyl-N-(4-butoxyphenethyl)aminoethyl]nitrobenzene.

(C)

Similarly, proceeding as in Part A and Part B above, but substituting 4-benzyloxy-3-nitrophenylethyltosylate for 3-nitrophenylethyltosylate, the following compounds (VI, A=BzO) are produced:
2-benzyloxy-5-(2-N-propyl-N-phenethylaminoethyl)nitrobenzene
2-benzyloxy-5-(2-N-ethyl-N-phenethylaminoethyl)nitrobenzene;
2-benzyloxy-5-[2-N-propyl-N-(4-benzyloxyphenethyl)aminoethyl]nitrobenzene;
2-benzyloxy-5-[2-N-butyl-N-(4-benzyloxyphenethyl)aminoethyl]nitrobenzene;
2-benzyloxy-5-[2-N-ethyl-N-(3-nitrophenyl)ethylaminoethyl]nitrobenzene;
2-benzyloxy-5-(2-N-propyl-N-phenylbutylaminoethyl)nitrobenzene;
2-benzyloxy-5-[2-N-ethyl-N-(3-nitrophenyl)methylaminoethyl]nitrobenzene;
2-benzyloxy-5-[2-N-butyl-N-(4-methylphenyl)ethylaminoethyl]nitrobenzene;
2-benzyloxy-5-[2-N-propyl-N-(4-aminophenethyl)aminoethyl]nitrobenzene;
2-benzyloxy-5-[2-N-propyl-N-(4-butylphenylethyl)aminoethyl]nitrobenzene;
2-benzyloxy-5-[2-N-propyl-N-(3-methoxyphenylethyl)aminoethyl]nitrobenzene; and
2-benzyloxy-5-[2-N-propyl-N-(4-butoxyphenethyl)aminoethyl]nitrobenzene.

PREPARATION 6

(Preparation of Compounds of Formula VII, Novel Intermediates of the Invention)

(Step 5)

(A)

To 10.1 g of 3-(2-N-propyl-N-phenethylaminoethyl)nitrobenzene (VI) in 200 ml of ethanol was added 1.0 g of Raney nickel and the solution heated to reflux. A solution of 10 ml of hydrazine hydrate in ethanol was slowly added. After filtration and evaporation, the mixture yielded 6.8 g of 3-(2-N-propyl-N-phenethylaminoethyl)aniline (VII, A=H) as an oil.

(B)

Similarly, proceeding as in Part A above, but substituting the compounds made in Preparation 5(B) above for 3-(2-N-propyl-N-phenethylaminoethyl)nitrobenzene, the following compounds are prepared:
3-(2-N-ethyl-N-phenethylaminoethyl)aniline;
3-(2-N-butyl-N-benzylaminoethyl)aniline;
3-[2-N-propyl-N-(4-benzyloxyphenethyl)aminoethyl]aniline;
3-[2-N-butyl-N-(4-benzyloxyphenethyl)aminoethyl]aniline;
3-[2-N-ethyl-N-(3-aminophenyl)ethylaminoethyl]aniline;
3-(2-N-propyl-N-phenylbutylaminoethyl)aniline;

3-[2-N-ethyl-N-(3-aminophenyl)methylaminoethyl]aniline;
3-[2-N-butyl-N-(4-methylphenyl)ethylaminoethyl]aniline;
3-[2-N-propyl-N-(4-aminophenethyl)aminoethyl]aniline;
3-[2-N-propyl-N-(4-butylphenyl)methylaminoethyl]aniline;
3-[2-N-propyl-N-(3-methoxyphenyl)ethylaminoethyl]aniline; and
3-[2-N-propyl-N-(4-butoxyphenethyl)aminoethyl]aniline.

(C)

Similarly, proceeding as in Part A and Part B above, but substituting the compounds prepared in Preparation 5(C) above for 3-(2-N-propyl-N-phenethylaminoethyl)-nitrobenzene, the following compounds (VII, A=BzO) are prepared:
2-benzyloxy-5-(2-N-propyl-N-phenethylaminoethyl)aniline;
2-benzyloxy-5-(2-N-ethyl-N-phenethylaminoethyl)aniline;
2-benzyloxy-5-[2-N-propyl-N-(4-benzyloxyphenethyl)aminoethyl]aniline;
2-benzyloxy-5-[2-N-butyl-N-(4-benzyloxyphenethyl)aminoethyl]aniline;
2-benzyloxy-5-[2-N-ethyl-N-(3-aminophenyl)ethylaminoethyl]aniline;
2-benzyloxy-5-(2-N-propyl-N-phenylbutylaminoethyl)aniline;
2-benzyloxy-5-[2-N-ethyl-N-(3-aminophenyl)methylaminoethyl]aniline;
2-benzyloxy-5-[2-N-butyl-N-(4-methylphenyl)ethylaminoethyl]aniline;
2-benzyloxy-5-[2-N-propyl-N-(4-aminophenethyl)aminoethyl]aniline;
2-benzyloxy-5-[2-N-propyl-N-(4-butylphenyl)methylaminoethyl]aniline;
2-benzyloxy-5-[2-N-propyl-N-(3-methoxyphenyl)ethylaminoethyl]aniline; and
2-benzyloxy-5-[2-N-propyl-N-(4-butoxyphenethyl)aminoethyl]aniline.

EXAMPLE 1

(Preparation of Compounds of Formula VIIIa)

(Step 6a)

(A)

3.4 g of sodium formate is added to 3.6 ml of acetyl chloride in 20 ml of THF at 0° C. and allowed to stand for 24 hr to form formic acetic anhydride. To this solution is added 10 g of 3-(2-N-propyl-N-phenethylaminoethyl)aniline in 50 ml of pyridine. The solution is allowed to stand at 0° C. for 12 hr, and is then added to water and extracted with $CH_2Cl_2$. The solvent is evaporated, and the residue is purified by silica gel chromatography to afford 3-(2-N-propyl-N-phenethylaminoethyl)formanilide (VIIIa, A=H).

(B)

Similarly, proceeding as in Part A above, but substituting the compounds prepared in Preparation 6(B) above for 3-(2-N-propyl-N-phenethylaminoethyl)aniline, the following compounds (VIIIa, A=H) are prepared:
3-(2-N-ethyl-N-phenethylaminoethyl)formanilide;
3-(2-N-butyl-N-benzylaminoethyl)formanilide;
3-[2-N-propyl-N-(4-benzyloxyphenethyl)aminoethyl]formanilide;
3-[2-N-butyl-N-(4-benzyloxyphenethyl)aminoethyl]formanilide;
3-[2-N-ethyl-N-(3-aminophenethyl)aminoethyl]formanilide;
3-(2-N-propyl-N-phenylbutylaminoethyl)formanilide;
3-[2-N-ethyl-N-(3-aminophenyl)methylaminoethyl]formanilide;
3-[2-N-butyl-N-(4-methylphenyl)ethylaminoethyl]formanilide;
3-[2-N-propyl-N-(4-aminophenethyl)aminoethyl]formanilide;
3-[2-N-propyl-N-(4-butylphenethyl)aminoethyl]formanilide;
3-[2-N-propyl-N-(3-methoxyphenethyl)aminoethyl]formanilide; and
3-[2-N-propyl-N-(4-butoxyphenethyl)aminoethyl]formanilide.

(C)

Similarly, proceeding as in Part A and Part B above, but substituting the compounds prepared in Preparation 6(C) for 3-(2-N-propyl-N-phenethylaminoethyl)aniline, the following compounds (VIIIa, A=BzO) are prepared:
2-benzyloxy-5-(2-N-propyl-N-phenethylaminoethyl)formanilide;
2-benzyloxy-5-(2-N-ethyl-N-phenethylaminoethyl)formanilide;
2-benzyloxy-5-[2-N-propyl-N-(4-benzyloxphenethyl)aminoethyl]formanilide;
2-benzyloxy-5-[2-N-butyl-N-(4-benzyloxyphenethyl)aminoethyl]formanilide;
2-benzyloxy-5-[2-N-ethyl-N-(3-aminophenethyl)aminoethyl]formanilide;
2-benzyloxy-5-(2-N-propyl-N-phenylbutylaminoethyl)formanilide;
2-benzyloxy-5-[2-N-ethyl-N-(3-aminophenyl)methylaminoethyl]formanilide;
2-benzyloxy-5-[2-N-butyl-N-(4-methylphenethyl)aminoethyl]formanilide;
2-benzyloxy-5-[2-N-propyl-N-(4-aminophenethyl)aminoethyl]formanilide;
2-benzyloxy-5-[2-N-propyl-N-(4-butylphenethyl)aminoethyl]formanilide;
2-benzyloxy-5-[2-N-propyl-N-(3-methoxyphenethyl)aminoethyl]formanilide; and
2-benzyloxy-5-[2-N-propyl-N-(4-butoxyphenethyl)aminoethyl]formanilide.

EXAMPLE 2

(Preparation of Compounds of Formula VIIIb)

(Step 6b)

(A)

3.5 g of 3-(2-N-propyl-N-phenethylaminoethyl)aniline in 20 ml of pyridine is treated with 1 ml of acetyl chloride at 0° C. The solution is added to water and extracted with $CH_2Cl_2$. The solvent is evaporated and the product 3-(2-N-propyl-N-phenethylaminoethyl)acetanilide (VIIIb, A=H) is purified by silica gel chromatography (HBr salt m.p. 212°-213° C.).

(B)

Similarly, proceeding as in Part A above, but substituting propanoyl chloride or butanoyl chloride for acetyl chloride, the following compounds are prepared:
3-(2-N-propyl-N-phenethylaminoethyl)propionanilide;
3-(2-N-propyl-N-phenethylaminoethyl)butyranilide.

(C)

Similarly, proceeding as in Part A above, but substituting the compounds prepared in Preparation 6(B) above for 3-(2-N-propyl-N-phenethylaminoethyl)aniline, the following compounds (VIIIb, A=H) are prepared:
3-(2-N-ethyl-N-phenethylaminoethyl)acetanilide;
3-(2-N-butyl-N-benzylaminoethyl)acetanilide;
3-[2-N-propyl-N-(4-benzyloxyphenethyl)aminoethyl]acetanilide;
3-[2-N-butyl-N-(4-benzyloxyphenethyl)aminoethyl]acetanilide;
3-[2-N-ethyl-N-(3-aminophenethyl)aminoethyl]acetanilide;
3-(2-N-propyl-N-phenylbutylaminoethyl)acetanilide;
3-[2-N-ethyl-N-(3-aminophenyl)methylaminoethyl]acetanilide;
3-[2-N-butyl-N-(4-methylphenyl)ethylaminoethyl]acetanilide;
3-[2-N-propyl-N-(4-aminophenethyl)aminoethyl]acetanilide;
3-[2-N-propyl-N-(4-butylphenylethyl)aminoethyl]acetanilide;
3-[2-N-propyl-N-(3-methoxyphenylethyl)aminoethyl]acetanilide; and
3-[2-N-propyl-N-(4-butoxyphenethyl)aminoethyl]acetanilide.

(D)

Similarly, proceeding as in Parts A, B, and C above, but substituting the compounds made in Preparation 6(C) for 3-(2-N-propyl-N-phenethylaminoethyl)aniline and propanoyl chloride or butanoyl chloride for acetyl chloride, the corresponding propionanilide and butyranilide derivatives (VIIIb, A=H) are prepared.

(E)

Similarly, proceeding as in Part A above, but substituting the compounds made in Preparation 6(C) for 3-(2-N-propyl-N-phenethylaminoethyl)aniline, the following compounds (VIIIb, A=BzO) are prepared:
2-benzyloxy-5-(2-N-propyl-N-phenethylaminoethyl)acetanilide;
2-benzyloxy-5-(2-N-ethyl-N-phenethylaminoethyl)acetanilide;
2-benzyloxy-5-[2-N-propyl-N-(4-benzyloxyphenethyl)aminoethyl]acetanilide;
2-benzyloxy-5-[2-N-butyl-N-(4-benzyloxyphenethyl)aminoethyl]acetanilide;
2-benzyloxy-5-[2-N-ethyl-N-(3-aminophenethyl)aminoethyl]acetanilide;
2-benzyloxy-5-(2-N-propyl-N-phenylbutylaminoethyl)acetanilide;
2-benzyloxy-5-[2-N-ethyl-N-(3-aminophenyl)methylaminoethyl]acetanilide;
2-benzyloxy-5-[2-N-butyl-N-(4-methylphenyl)ethylaminoethyl]acetanilide;
2-benzyloxy-5-[2-N-propyl-N-(4-aminophenethyl)aminoethyl]acetanilide;
2-benzyloxy-5-[2-N-propyl-N-(4-butylphenethyl)aminoethyl]acetanilide;
2-benzyloxy-5-[2-N-propyl-N-(3-methoxyphenylethyl)aminoethyl]acetanilide; and
2-benzyloxy-5-[2-N-propyl-N-(4-butoxyphenethyl)aminoethyl]acetanilide.

(F)

Similarly, proceeding as in Parts B and E above, the corresponding 2-benzyloxy-propionanilide and butyranilide derivatives (VIIb, A=BzO) are prepared.

EXAMPLE 3

(Preparation of Compounds of Formula VIIIc)

(Step 6c)

(A)

A solution of 2.2 g of 3-(2-N-propyl-N-phenethylaminoethyl)aniline in 10 ml 2:1 water/acetic acid was treated with 1.5 g of potassium cyanate in 5 ml of water. The mixture was then made basic with NH$_4$OH and extracted with CH$_2$Cl$_2$. The CH$_2$Cl$_2$ was evaporated, and the residue dissolved in methanol. Then, 48% aqueous HBr or HCl was added until the solution was acidic. The product, 3-(2-N-propyl-N-phenethylaminoethyl)ureidobenzene.HBr, (VIIIc, A=H) was precipitated from the solution with Et$_2$O.

(B)

Similarly, proceeding as in Part A above, but substituting the compounds prepared in Preparation 6(B) above for 3-(2-N-propyl-N-phenethylaminoethyl)aniline, the following compounds (VIIIc, A=H) are prepared:
3-(2-N-ethyl-N-phenethylaminoethyl)ureidobenzene.HBr;
3-(2-N-butyl-N-benzylaminoethyl)ureidobenzene.HBr;
3-[2-N-propyl-N-(4-benzyloxyphenethyl)aminoethyl]ureidobenzene.HBr;
3-[2-N-butyl-N-(4-benzyloxyphenethyl)aminoethyl]ureidobenzene.HBr;
3-[2-N-ethyl-N-(3-ureidophenyl)ethylaminoethyl]ureidobenzene.HBr;
3-(2-N-propyl-N-phenylbutylaminoethyl)ureidobenzene.HBr;
3-[2-N-ethyl-N-(3-ureidophenyl)methylaminoethyl]ureidobenzene.HBr;
3-[2-N-butyl-N-(4-methylphenyl)ethylaminoethyl]ureidobenzene.HBr;
3-[2-N-propyl-N-(4-ureidophenethyl)aminoethyl]ureidobenzene.HBr;
3-[2-N-propyl-N-(4-butylphenylethyl)aminoethyl]ureidobenzene.HBr;
3-[2-N-propyl-N-(3-methoxyphenylethyl)aminoethyl]ureidobenzene.HBr; and
3-[2-N-propyl-N-(4-butoxyphenethyl)aminoethyl]ureidobenzene.HBr.

(C)

Similarly, proceeding as a Part A and Part B above, but substituting the compounds prepared in Preparation 6(C) for 3-(2-N-propyl-N-phenethylaminoethyl)aniline, the following compounds (VIIIc, A=Bz0) are produced:
2-benzyloxy-5-(2-N-propyl-N-phenethylaminoethyl)ureidobenzene.HBr;

2-benzyloxy-5-(2-N-ethyl-N-phenethylaminoethyl-
)ureidobenzene.HBr;
2-benzyloxy-5-[2-N-propyl-N-(4-benzyloxyphenethyl-
)aminoethyl]ureidobenzene.HBr;
2-benzyloxy-5-[2-N-butyl-N-(4-benzyloxyphenethyl-
)aminoethyl]ureidobenzene.HBr;
2-benzyloxy-5-[2-N-ethyl-N-(3-ureidophenyl)e-
thylaminoethyl]ureidobenzene.HBr;
2-benzyloxy-5-(2-N-propyl-N-phenylbutylaminoethyl-
)ureidobenzene.HBr;
2-benzyloxy-5-[2-N-ethyl-N-(3-ureidophenyl)me-
thylaminoethyl]ureidobenzene.HBr;
2-benzyloxy-5-[2-N-butyl-N-(4-methylphenyl)e-
thylaminoethyl]ureidobenzene.HBr;
2-benzyloxy-5-[2-N-propyl-N-(4-ureidophenethyl-
)aminoethyl]ureidobenzene.HBr;
2-benzyloxy-5-[2-N-propyl-N-(4-butylphenethyl-
)aminoethyl]ureidobenzene.HBr;
2-benzyloxy-5-[2N-propyl-N-(3-methoxyphenylethyl-
)aminoethyl]ureidobenzene.HBr; and
2-benzyloxy-5-[2-N-propyl-N-(4-butoxyphenethyl-
)aminoethyl]ureidobenzene.HBr.

EXAMPLE 4

(Preparation of Compounds of Formula VIIId)

(Step 6d)

(A)

A solution of 2.2 g of 3-(2-N-propyl-N-phene-thylaminoethyl)aniline in 10 ml of 2:1 water/acetic acid is treated with 1.1 g of methyl isocyanate in 5 ml of water. The mixture is made basic with $NH_4OH$ and extracted with $CH_2Cl_2$. The solvent is evaporated to afford 1-[3-(2-N-propyl-N-phenethylaminoethyl)-phenyl]-3-methylurea (VIIId, A=H).

(B)

Similarly, proceeding as in Part A above, but substituting ethylisocyanate or propylisocyanate for methyl isocyanate, the following compounds (VIIId, A=H) are prepared:
1-[3-(2-N-propyl-N-phenethylaminoethyl)phenyl]-3-ethylurea;
1-[3-(2-N-propyl-N-phenethylaminoethyl)phenyl]-3-propylurea.

(C)

Similarly, proceeding as a Part A above, but substituting the compounds prepared in Preparation 6(B) above for 3-(2-N-propyl-N-phenethylaminoethyl)aniline, the following compounds (VIIId, A=H) are prepared:
1-[3-(2-N-ethyl-N-phenethylaminoethyl)phenyl]-3-methylurea;
1-[3-(2-N-butyl-N-benzylaminoethyl)phenyl]-3-methylurea;
1-(3-[2-N-propyl-N-(4-benzyloxyphenethyl)aminoe-thyl]phenyl]-3-methylurea;
1-(3-[2-N-butyl-N-(4-benzyloxyphenethyl)aminoethyl]-phenyl]-3-methylurea;
1-(3-[2-N-ethyl-N-(3-methylureidophenyl)ethylaminoe-thyl]phenyl]-3-methylurea;
1-[3-(2-N-propyl-N-phenylbutylaminoethyl)phenyl]-3-methylurea;
1-(3-[2-N-ethyl-N-(3-methylureidophenyl)me-thylaminoethyl]phenyl)-3-methylurea;
1-(3-[2-N-butyl-N-(4-methylphenyl)ethylaminoethyl]-phenyl)-3-methylurea;
1-(3-[2-N-propyl-N-(4-methylureidophenethyl)aminoe-thyl]phenyl)-3-methylurea;
1-(3-[2-N-propyl-N-(4-butylphenylethyl)aminoethyl]-phenyl)-3-methylurea;
1-(3-[2-N-propyl-N-(3-methoxyphenylethyl)aminoe-thyl]phenyl)-3-methylurea; and
1-(3-[2-N-propyl-N-(4-butoxyphenethyl)aminoethyl]-phenyl)-3-methylurea.

(D)

Similarly, proceeding as in Part A above, but substituting the compounds made in Preparation 6(C) for 3-(2-N-propyl-N-phenethylaminoethyl)aniline, the following compounds (VIIId, A=Bz0) are prepared:
1-[2-benzyloxyl-5-(2-N-propyl-N-phenethylaminoe-thyl)phenyl]-3-methylurea;
1-[2-benzyloxy-5-(2-N-ethyl-N-phenethylaminoethyl)-phenyl]-3-methylurea;
1-(2-benzyloxy-5-[2-N-propyl-N-(4-benzyloxyphene-thyl)aminoethyl]phenyl)-3-methylurea;
1-(2-benzyloxy-5-[2-N-butyl-N-(4-benzyloxyphenethyl-)aminoethyl]phenyl)-3-methylurea;
1-(2-benzyloxy-5-[2-N-ethyl-N-(3-methylureidophenyl-)ethylaminoethyl]phenyl)-3-methylurea;
1-[2-benzyloxy-5-(2-N-propyl-N-phenylbutylaminoe-thyl)phenyl]-3-methylurea;
1-(2-benzyloxy-5-[2-N-ethyl-N-(3-methylureido-phenyl)methylaminoethyl]phenyl)-3-methylurea;
1-(2-benzyloxy-5-[2-N-butyl-N-(4-methylphenyl)e-thylaminoethyl]phenyl)-3-methylurea;
1-(2-benzyloxy-5-[2-N-propyl-N-(4-methylureido-phenethyl)aminoethyl]phenyl)-3-methylurea;
1-(2-benzyloxy-5-[2-N-propyl-N-(4-butylphenethyl-)aminoethyl]phenyl)-3-methylurea;
1-(2-benzyloxy-5-[2-N-propyl-N-(3-methoxyphenyle-thyl)aminoethyl]phenyl)-3-methylurea; and
1-(2-benzyloxy-5-[2-N-propyl-N-(4-butoxyphenethyl-)aminoethyl]phenyl)-3-methylurea.

(E)

Similarly, proceeding as in Part B above, but substituting the compounds made in Preparation 6(C) for 3-(2-N-propyl-N-phenethylaminoethyl)aniline, the corresponding 3-ethylurea and 3-propylurea compounds (VIIId, A=BzO) are prepared.

EXAMPLE 5

(Preparation of Compounds of Formula I wherein $R_3$ is Hydroxy)

(Step 7)

(A)

A solution of 3.3 g of 2-benzyloxy-5-(2-N-propyl-N-phenethylaminoethyl)ureidobenzene.HBr (VIIIc, A=BzO) in 150 ml of methanol was hydrogenated with 0.5 g of 10% Pd-C for 6 hr. at 2 atmospheres and 60° C. Filtration and evaporation afforded an oil which was dissolved in methanol and acidified with hydrogen bromide. Addition of $Et_2O$ precipitated the HBr salt, 2-hydroxy-5-(2-N-propyl-N-phenethylaminoethyl-)ureidobenzene.HBr (I.HBr).

Similarly, proceeding as above but substituting hydrogen chloride for hydrogen bromide, the hydrochloride salts are prepared.

(B)

Similarly, proceeding as in Part A above, but substituting the compounds prepared in Example 1(C) for 2-benzyloxy-5-(2-N-propyl-N-phenethylaminoethyl)ureidobenzene.HBr, the following compounds are prepared:
2-hydroxy-5-(2-N-propyl-N-phenethylaminoethyl)formanilide;
2-hydroxy-5-(2-N-ethyl-N-phenethylaminoethyl)formanilide;
2-hydroxy-5-[2-N-propyl-N-(4-hydroxyphenethyl)aminoethyl]formanilide;
2-hydroxy-5-[2-N-butyl-N-(4-hydroxyphenethyl)aminoethyl]formanilide;
2-hydroxy-5-[2-N-ethyl-N-(3-aminophenyl)ethylaminoethyl]formanilide;
2-hydroxy-5-(2-N-propyl-N-phenylbutylaminoethyl)formanilide;
2-hydroxy-5-[2-N-ethyl-N-(3-aminophenyl)methylaminoethyl]formanilide;
2-hydroxy-5-[2-N-butyl-N-(4-methylphenyl)ethylaminoethyl]formanilide;
2-hydroxy-5-[2-N-propyl-N-(4-aminophenethyl)aminoethyl]formanilide;
2-hydroxy-5-[2-N-propyl-N-(4-butylphenylethyl)aminoethyl]formanilide;
2-hydroxy-5-[2-N-propyl-N-(3-methoxyphenylethyl)aminoethyl]formanilide; and
2-hydroxy-5-[2-N-propyl-N-(4-butoxyphenethyl)aminoethyl]formanilide.

(C)

Similarly, proceeding as in Part A above, but substituting the compounds prepared in Example 2(E) for 2-benzyloxy-5-(2-N-propyl-N-phenethylaminoethyl)ureidobenzene.HBr, the following compounds are produced:
2-hydroxy-5-(2-N-propyl-N-phenethylaminoethyl)acetanilide;
2-hydroxy-5-(2-N-ethyl-N-phenethylaminoethyl)acetanilide;
2-hydroxy-5-[2-N-propyl-N-(4-hydroxyphenethyl)aminoethyl]acetanilide;
2-hydroxy-5-[2-N-butyl-N-(4-hydroxyphenethyl)aminoethyl]acetanilide;
2-hydroxy-5-[2-N-ethyl-N-(3-aminophenyl)ethylaminoethyl]acetanilide;
2-hydroxy-5-(2-N-propyl-N-phenylbutylaminoethyl)acetanilide;
2-hydroxy-5-[2-N-ethyl-N-(3-aminophenyl)methylaminoethyl]acetanilide;
2-hydroxy-5-[2-N-butyl-N-(4-methylphenyl)ethylaminoethyl]acetanilide;
2-hydroxy-5-[2-N-propyl-N-(4-aminophenethyl)aminoethyl]acetanilide;
2-hydroxy-5-[2-N-propyl-N-(4-butylphenethyl)aminoethyl]acetanilide;
2-hydroxy-5-[2-N-propyl-N-(3-methoxyphenylethyl)aminoethyl]acetanilide; and
2-hydroxy-5-[2-N-propyl-N-(4-butoxyphenethyl)aminoethyl]acetanilide.

(D)

Similarly, proceeding as in Part A above, but substituting the compounds prepared in Example 2(F) for 2-benzyloxy-5-(2-N-propyl-N-phenethylaminoethyl)ureidobenzene.HBr, the corresponding propionanilide and butyranilide derivatives (VIIIb, A=H) are prepared.

(E)

Similarly, proceeding as in Part A above, but substituting the compounds prepared in Example 3(C) for 2-benzyloxy-5-(2-N-propyl-N-phenethylaminoethyl)ureidobenzene.HBr, the following compounds are prepared:
2-hydroxy-5-(2-N-propyl-N-phenethylaminoethyl)ureidobenzene.HBr;
2-hydroxy-5-(2-N-ethyl-N-phenethylaminoethyl)ureidobenzene.HBr;
2-hydroxy-5-[2-N-propyl-N-(4-hydroxyphenethyl)aminoethyl]ureidobenzene.HBr;
2-hydroxy-5-[2-N-butyl-N-(4-hydroxyphenethyl)aminoethyl]ureidobenzene.HBr;
2-hydroxy-5-[2-N-ethyl-N-(3-aminophenyl)ethylaminoethyl]ureidobenzene.HBr;
2-hydroxy-5-(2-N-propyl-N-phenylbutylaminoethyl)ureidobenzene.HBr;
2-hydroxy-5-[2-N-ethyl-N-(3-aminophenyl)methylaminoethyl]ureidobenzene.HBr;
2-hydroxy-5-[2-N-butyl-N-(4-methylphenyl)ethylaminoethyl]ureidobenzene.HBr;
2-hydroxy-5-[2-N-propyl-N-(4-aminophenethyl)aminoethyl]ureidobenzene.HBr;
2-hydroxy-5-[2-N-propyl-N-(4-butylphenethyl)aminoethyl]ureidobenzene.HBr;
2-hydroxy-5-[2-N-propyl-N-(3-methoxyphenylethyl)aminoethyl]ureidobenzene.HBr; and
2-hydroxy-5-[2-N-propyl-N-(4-butoxyphenethyl)aminoethyl]ureidobenzene.HBr.

(F)

Similarly, proceeding as in Part A above, but substituting the compounds prepared in Example 4(D) for 2-benzyloxy-5-(2-propyl-N-phenethylaminoethyl)ureidobenzene.HBr, the following compounds are prepared:
1-[2-hydroxy-5-(2-N-propyl-N-phenethylaminoethyl)phenyl]-3-methylurea;
1-[2-hydroxy-5-(2-N-ethyl-N-phenethylaminoethyl)phenyl]-3-methylurea;
1(2-hydroxy-5-[2-N-propyl-N-(4-hydroxyphenethyl)aminoethyl]phenyl-3-methylurea;
1-(2-hydroxy-5-[2-N-butyl-N-(4-hydroxyphenethyl)aminoethyl]phenyl)-3-methylurea;
1-(2-hydroxy-5-[2-N-ethyl-N-(3-aminophenyl)ethylaminoethyl]phenyl)-3-methylurea;
1-[2-hydroxy-5-(2-N-propyl-N-phenylbutylaminoethyl)phenyl]-3-methylurea;
1-(2-hydroxy-5-[2-N-ethyl-N-(3-aminophenyl)methylaminoethyl]phenyl)-3-methylurea;
1-(2-hydroxy-5-[2-N-butyl-N-(4-methylphenyl)ethylaminoethylphenyl)-3-methylurea;
1-(2-hydroxy-5-[2-N-propyl-N-(4-aminophenethyl)aminoethyl]phenyl)-3-methylurea;
1-(2-hydroxy-5-[2-N-propyl-N-(4-butylphenyl)aminoethyl]phenyl)-3-methylurea;
1-(2-hydroxy-5-[2-N-propyl-N-(3-methoxyphenylethyl)aminoethyl]phenyl)-3-methylurea; and
1-(2-hydroxy-5-[2-N-propyl-N-(4-butoxyphenethyl)aminoethyl]phenyl)-3-methylurea.

(G)

Similarly, proceeding as in Part A above, but substituting the compounds prepared in Example 4(E) for 2-benzyloxy-5-(2-N-propyl-N-phenethylaminoethyl-)ureidobenzene.HBr, the corresponding 3-ethylurea and 3-propylurea derivatives are prepared.

EXAMPLE 6

(Preparation of Salts From Free Bases)

8.0 g of 3-(2-N-propyl-N-phenethylaminoethyl-)ureidobenzene is dissolved in methanol and acidified with methanolic HCl. The precipitate is washed with Et$_2$O to give 7.0 g of the hydrochloride salt of 3-(2-N-propyl-N-phenethylaminoethyl)ureidobenzene.

In a similar manner, all compounds of formula I in base form prepared in accordance with the methods described above can be converted to their pharmaceutically acceptable acid addition salts by treatment with the appropriate acid, for example, HBr, sulfuric acid, nitric acid, phosphoric acid, acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

EXAMPLE 7

(Preparation of Free Bases From Salts)

A solution of 3.5 g of 3-(2-N-propyl-N-phenethylaminoethyl)ureidobenzene.HCl in water (50 ml) is adjusted to pH 12 with HN$_4$OH solution and extracted with methylene chloride. The methylene chloride is then evaporated to afford 3 g of 3-(2-N-propyl-N-phenethylaminoethyl)ureidobenzene as the free base.

In a similar manner, all acid addition salts of compounds of formula I prepared in accordance with the methods described above can be converted to their free base form.

EXAMPLE 8

(Formulations)

The following example illustrates the preparation of representative pharmaceutical formulations containing an active compound of Formula I, e.g., 3-(2-N-propyl-N-phenethylaminoethyl)ureidobenzene.

Intraocular Solution

Active compound: 0.10 g
Benzalkonium Chloride: 0.01 g
EDTA: 0.10 g
Sodium Phosphate Buffer qs: pH 7.4
2% Boric acid solution qs: 100 ml The active compound is dissolved in 2% Boric acid solution, benzalkonium chloride, sodium phosphate buffer and ethylenediaminetetraacetic acid (EDTA). The solution is then filtered through a 0.2 micron membrane filter and packaged under sterile conditions.

Intraocular Ointment

Active Compound: 1 g
Benzalkonium Chloride: 0.1 g
EDTA: 1.0 g
White Wax: 50 g
Petrolatum: 950 g The wax is melted over a water bath. The petrolatum is then added and heated until it liquifies. The mixture is then cooled and stirred until it congeals. The remaining ingredients are then added as micronized powders and the mixture packaged under sterile conditions.

EXAMPLE 9

(Ocular Irritation Test)

Each studied compound is tested individually on a single animal by administering, at the same time, into one eye of the animal the ophthalmic solution with the test compound as an active ingredient and to the other eye only vehicle ophthalmic solution. An irritation, if any, caused by tested compounds is compared to the non-irritating effect of the vehicle ophthalmic solution applied to the other eye. Irritation is measured by the number of blinks of each eye during the same time period. Tests are performed on rats, dogs and monkeys.

Ophthalmic solutions with compounds of the invention as the active ingredient are prepared at the concentrations of 0.01% to 0.5%. One drop of the test ophthalmic solution with active ingredient is administered directly into the conjuctival sack of the rat's left eye. At the same time one drop of vehicle is administered to the conjunctival sack of the rat's right eye.

Irritation of each eye is measured by counting the number of blinks for one minute after the application. The results are expressed as the mean number of blinks±standard error per eye. The mean number of blinks/minute is averaged for the vehicle treatment and compared to the drug treated eye. Each compound is tested similarly in mongrel dogs and rhesus monkeys.

The compounds of this invention do not elicit any irritation of the eyes in any of the three species at any concentration which is used for testing (i.e., 0.12–0.5%) and their effects are comparable to the effect of the vehicle ophthalmic solution without any drug added.

EXAMPLE 10

(Reduction of Intraocular Pressure)

This example illustrates the effect of compounds of the current invention on intraocular pressure (IOP).

Two groups of normal albino white New Zealand rabbits are used for this study.
Control group: 4 animals
Experimental group: 8 animals Experimental schedule At time 0, the intraocular pressure of both eyes of each animal in control and experimental groups is determined.

All animals receive the treatment either with saline (control group) or the tested compound (experimental group) immediately after the 0 hour intraocular pressure reading. The control group receives 50 μl of vehicle in both eyes. Experimental animals receive 50 μl of vehicle in the left eyes and 50 μl of 1% solution of tested compound in the right eyes.

Intraocular pressure is measured at 30 minutes, 1, 2, and 4 hours.

Experimental Procedure

The effects of tested drug on intraocular pressure of the rabbit is determined using a Digilab Model 30D pneuma-tonometer. Initial IOP readings are obtained in all animals after the administration of 50 μl of 0.5% Opthaine (proparacaine hydrochloride). A group of 4 rabbits serves as control and is treated with 50 μl of saline in both eyes. Eight additional rabbits receive 50 μl of test drug in the right eye, and 50 μl of drug vehicle is administered in the contralateral left eye. IOP readings are made 30 minutes, 1 hours, 2 hours, and 4 hours after drug administration. Rabbits are observed for any signs of ocular irritation.

This procedure permits the comparison of drug treated eye with the contralateral vehicle treated eye, and also with saline treated eye. For purposes of statistical analysis comparisons are made between the drug treated IOP values and vehicle treated contralateral eyes and also the saline treated IOP values.

What is claimed is:

1. The compound 3-[2-N-propyl-N-(3-ureidophenethyl)aminoethyl]ureidobenzene.

* * * * *